United States Patent [19]

O'Lenick, Jr.

[11] Patent Number: 6,008,397

[45] Date of Patent: Dec. 28, 1999

[54] SILICONE FLUORO ESTERS

[75] Inventor: Anthony J. O'Lenick, Jr., Dacula, Ga.

[73] Assignee: Hansotech Inc., Woodbury, N.Y.

[21] Appl. No.: 09/323,412

[22] Filed: Jun. 1, 1999

[51] Int. Cl.$^6$ ...................................................... C07F 7/08
[52] U.S. Cl. ............................................................ 556/437
[58] Field of Search ................................... 556/437, 440; 554/77

[56] References Cited

U.S. PATENT DOCUMENTS

| | | | |
|---|---|---|---|
| 5,296,625 | 3/1994 | O'Lenick | 556/437 |
| 5,446,183 | 8/1995 | O'Lenick, Jr. | 556/437 |
| 5,475,125 | 12/1995 | O'Lenick, Jr. | 556/437 |
| 5,733,533 | 3/1998 | O'Lenick, Jr. et al. | 424/64 |

*Primary Examiner*—Paul F. Shaver

[57] ABSTRACT

The invention discloses novel fluoro esters made by reacting (a) a carboxy silicone, and (b) the hydroxyl group of fluoro alcohol. The compounds of the invention by virtue of (i) the silicone group, (ii) the fluoro group and (iii) the polyoxyalkylene present in the compound are extremely efficient skin care compounds used in topical treatment of skin.

15 Claims, No Drawings

SILICONE FLUORO ESTERS

The invention discloses novel fluoro esters of silicone compounds which an ester linkage, and a silicone polymer. Compounds of the invention are made by reacting (a) a carboxy silicone, and (b) fluoro alcohol to form an ester. Compounds of the invention by virtue of (i) the silicone group, (ii) the ester group and (iii) the fluoro containing group all contribute to a unique highly effective spreadable lubricating coating that have an outstanding feel on skin.

The reaction used to prepare the compounds of the present invention is an esterification of a carboxy silicone and fluoro alcohol. The resulting ester provides effective highly spreadable coatings that have an outstanding feel on skin.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

Silicone oils do not provide ultra violet absorption, and consequently protection from the damaging effects of the sun. The aromatic compounds that provide this type of absorbance are not durable to the surfaces of substrates.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

OBJECT OF THE INVENTION

It is the object of the present invention to provide an effective highly spreadable coatings that have an outstanding feel on skin. The presence of silicone in the molecule gives superior durability to these substrates, the presence of the fluoro group gives superior spreadability on the hair and skin. The presence of the ester linkage between the silicone and aromatic group results in a linkage which will biodegrade rapidly in waste water, making the compound less persistent in the waste water stream.

The formation of the ester linkage and the incorporation of the fluoro group into the silicone of the present invention is accomplished by an esterification reaction of a carboxy silicone and a fluoro alcohol.

SUMMARY OF THE INVENTION

The compounds of this invention are made by the esterification of a carboxy silicone compound and fluoro alcohol. In order to obtain a molecule with the desired attributes, the amount of fluorine is controlled by selection of the particular fluoro alcohol used in the reaction. Only if the compounds are specifically selected will compounds useful in the preparation of the compounds of the present invention be obtained.

Specifically, the compounds of the present invention are esters compounds which is prepared by the esterification reaction of:

(a) a silicone carboxylate conforming to the following structure:

$$R'-\underset{\underset{Me}{|}}{\overset{\overset{Me}{|}}{Si}}-O-\left[\underset{\underset{R}{|}}{\overset{\overset{Me}{|}}{Si}}-O\right]_o-\left[\underset{\underset{R^1}{|}}{\overset{\overset{Me}{|}}{Si}}-O\right]_q-\underset{\underset{Me}{|}}{\overset{\overset{Me}{|}}{Si}}-R'$$

wherein;
Me is methyl:
R and R' are $CH_3$ or $-(CH_2)_3-O-(EO)_a-(PO)_b-(EO)_c-C(O)-R''-C(O)-OH$;
   with the proviso that both R and R' are not $CH_3$;
R" is selected from $-CH_2-CH_2-$;  $-CH=CH-$;  $-CH_2-C(R^7)-H$;

and ;

$R^7$ is alkyl having from 1 to 20 carbon atoms;
$R^1$ is selected from lower alkyl $CH_3(CH)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100.
q is an integer ranging from 0 to 500. and
(b) a fluoro which conforms to the following structure:

$$CF_3(CF_2)_a-(CH_2)_2OH$$

a is an integer ranging from 3 to 17.
Compounds of the present invention conform to the following structure:

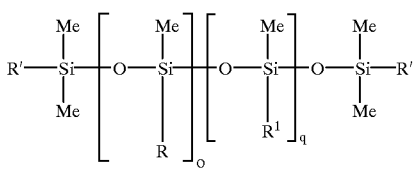

wherein;

Me is methyl;

R and R' are $CH_3$ or $-(CH_2)_3-O-(EO)_a-(PO)_b-(EO)_c-C(O)-R''-C(O)-OR^2$;

with the proviso that both R and R' are not $CH_3$;

R" is selected from

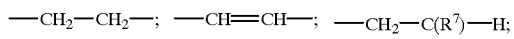

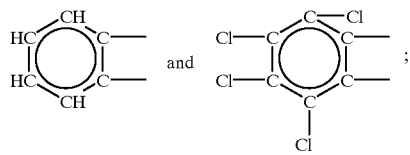

$R^7$ is alkyl having from 1 to 20 carbon atoms;
$R^1$ is selected from lower alkyl $CH_3(CH)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500;
$R^2$ is;

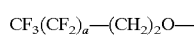

$CF_3(CF_2)_a-(CH_2)_2O-$ a is an integer ranging from 3 to 17.

EXAMPLES

The compounds of the present invention are prepared by the reaction of a carboxy silicone compound and fluoro alcohol. Examples of suitable reactants are as follows;

All percentages given are based upon percent by weight, based upon the total weight of the entire batch. All temperatures are degrees C.

Reactants

Fluorine Containing Alcohols

Fluorine containing alcohols are commercially available from a variety of suppliers, most importantly DuPonte Performance Products Division. They conform to the following structure:

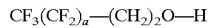

$CF_3(CF_2)_a-(CH_2)_2O-H$ a is ranges from 3 to 17.

| Reactant Example Number | a Value | Molecular Weight | % F |
|---|---|---|---|
| 1 | 3 | 264 | 64.7 |
| 2 | 5 | 364 | 67.8 |
| 3 | 7 | 464 | 69.6 |

-continued

| Reactant Example Number | a Value | Molecular Weight | % F |
|---|---|---|---|
| 4 | 9 | 564 | 70.7 |
| 5 | 11 | 664 | 71.5 |
| 6 | 13 | 764 | 72.1 |
| 7 | 15 | 864 | 72.5 |
| 8 | f7 | 964 | 72.9 |

Carboxy Reactants

The carboxy silicone compounds useful as raw materials in the preparation of the compounds of the present invention are disclosed in U.S. Pat. No. 5,296,625 to O'Lenick, Jr. et al, incorporated herein by reference.

PREFERRED EMBODIMENTS

In another preferred embodiment x+y+z is greater than zero.

In another preferred embodiment R" is $-CH_2-CH_2-$.

In another preferred embodiment R" is $-CH_2-C(R^7)-H$.

In another preferred embodiment R" is

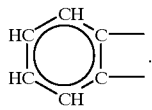

In another preferred embodiment R" is

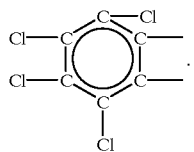

In another preferred embodiment a is 3.

In another preferred embodiment a is 5.

In another preferred embodiment a is 7.

In another preferred embodiment a is 9.

In another preferred embodiment a is 11.

In another preferred embodiment a is 13.

In another preferred embodiment a is 15.

In another preferred embodiment a is 17.

EXAMPLES

Dimethicone Carboxylate Compounds

Dimethicone Carboxylate compounds are disclosed in U.S. Pat. No. 5,296,625 incorporated herein by reference. They marketed by Siltech Corporation, Toronto Canada under the Silube trade name. The compounds conform to the following structure;

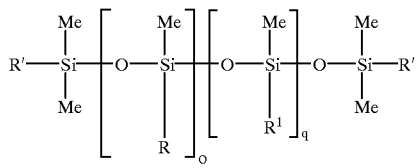

wherein;

Me is methyl;

R and R' are $CH_3$ or $-(CH_2)_3-O-(EO)_a-(PO)_b-(EO)_c-C(O)-R''-C(O)-OH$;

with the proviso that both R and R' are not $CH_3$;

R" is selected from

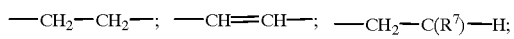
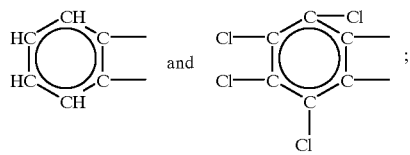

$R^7$ is alkyl having from 1 to 20 carbon atoms;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

The carboxy reactants are defined in O'Lenick U.S. Pat. No. 5,296,625 incorporated herein by reference, examples 15–32.

R" Definition

I) O'Lenick Reactant Example I (Succinic Anhydride)
R" is $-H_2C-CH_2-$

II) O'Lenick Reactant Example II (Alkyl Succinic Anhydride)
R" is

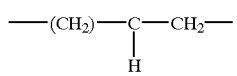

III) O'Lenick Reactant Example III (Alkyl Succinic Anhydride)
R" is

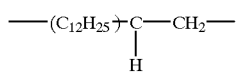

IV) O'Lenick Reactant Example IV (Alkyl Succinic Anhydride)
R" is

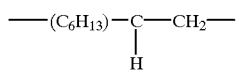

V) O'Lenick Reactant Example V (Alkyl Succinic Anhydride)
R" is

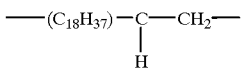

VI) O'Lenick Reactant Example VI (Alkyl Succinic Anhydride)
R" is

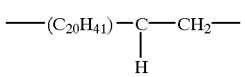

VII) O'Lenick Reactant Example VII (Maleic Anhydride)
R" is $-HC=CH-$

VIII) O'Lenick Reactant Example VIII (Phthalic Anhydride)
R" is

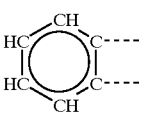

IX) O'Lenick Reactant Example IX (Tetrachlorophthalic anhydride)
R" is

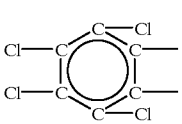

Compounds of the Present Invention

General Reaction Conditions:

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240° C. under an inert nitrogen blanket. The nitrogen blanket preserves the color. Preferred temperature range is between 180 and 210° C. Water is removed from the reaction which is done using a nitrogen sparge or vacuum.

EXAMPLES

General Procedure

Into a suitable round bottom, three neck flask equipped with a Dean Stark trap, a thermometer and a nitrogen sparge is added the specified number of grams of the carboxy silicone and the specified number of grams of fluoro alcohol and 0.25% of total weight of the batch of catalyst. The reaction mass is blanketed with nitrogen, and heated to 180 and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

Example 9

Into a suitable round bottom, three neck flask equipped with a Dean Stark trap, a thermometer and a nitrogen sparge is added 2,450 grams of the carboxy silicone (O'Lenick example 15), 264.0 grams of fluoro alcohol Example 1, and 0.25% of total weight of the batch of catalyst. The reaction mass is blanketed with nitrogen, and heated to 180 and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

Example 10–18

Example 9 is repeated only this time substituting the specified number of grams of the specified carboxy silicone for the carboxy silicone specified and the substituting the specified number of grams of the specified fluoro alcohol.

Note: In the below table Gms. is grams

| | Carboxy Silicone Compound | | | Fluoro Alcohol | |
|---|---|---|---|---|---|
| | R" | O'Lenick | | | |
| Example | Definition | Example | Grams | Example | Grams |
| 10 | I | 15 | 2,429.0 | 1 | 264.0 |
| 11 | II | 16 | 2,147.0 | 2 | 364.0 |
| 12 | III | 17 | 5,398.0 | 3 | 464.0 |
| 13 | IV | 18 | 533.0 | 4 | 564.0 |
| 14 | V | 19 | 4,723.0 | 5 | 664.0 |
| 15 | VI | 20 | 3,083.0 | 6 | 764.0 |
| 16 | VII | 21 | 3,648.8 | 7 | 864.0 |
| 17 | VIII | 22 | 1,722.4 | 8 | 964.0 |
| 18 | IX | 23 | 1,288.0 | 1 | 264.0 |

The compounds of the invention provide thin films when applied to hair and skin. They are highly lubricious and provide outstanding wet comb properties. Additionally, the compounds are mild to the skin and eyes making them outstanding additives to a variety of personal care formulations. These formulations include shampoos, conditioners, bubble bath compounds and skin care emulsions.

What is claimed:

1. A compound conforming to the following structure:

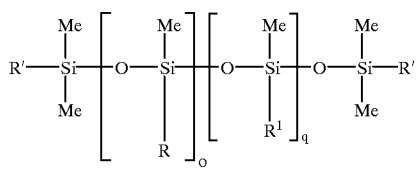

wherein;

Me is methyl;

R and R' are $CH_3$ or $-(CH_2)_3-O-(EO)_a-(PO)_b-(EO)_c-C(O)-R''-C(O)-OR^2$;

with the proviso that both R and R' are not $CH_3$;

R" is selected from

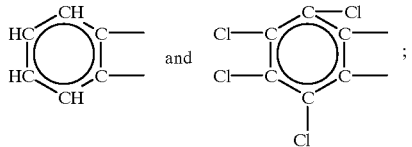

$R^7$ is alkyl having from 1 to 20 carbon atoms:

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500;

$R^2$ is;

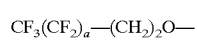

a is an integer ranging from 3 to 17.

2. A compound of claim 1 wherein R" is $-CH_2-CH_2-$.

3. A compound of claim 1 wherein R" is $-CH_2-C(R^7)-H$.

4. A compound of claim 1 wherein R" is

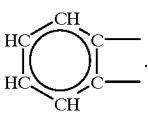

5. A compound of claim 1 wherein R" is

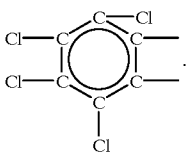

6. A compound of claim 3 wherein $R^7$ is alkyl having from 6 to 20 carbon atoms.

7. A compound of claim 3 wherein $R^7$ is alkyl having from 12 to 20 carbon atoms.

8. A compound of claim 1 wherein a is 3.
9. A compound of claim 1 wherein a is 5.
10. A compound of claim 1 wherein a is 7.
11. A compound of claim 1 wherein a is 9.
12. A compound of claim 1 wherein a is 11.
13. A compound of claim 1 wherein a is 13.
14. A compound of claim 1 wherein a is 15.
15. A compound of claim 1 wherein a is 17.

* * * * *